(12) United States Patent
Forsberg et al.

(10) Patent No.: US 7,648,493 B2
(45) Date of Patent: Jan. 19, 2010

(54) METHOD AND APPARATUS FOR LOCATING VASCULAR PUNCTURES

(75) Inventors: Andrew Thomas Forsberg, Minneapolis, MN (US); Loran Paprocki, St. Louis Park, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 929 days.

(21) Appl. No.: 10/827,714

(22) Filed: Apr. 20, 2004

(65) Prior Publication Data

US 2005/0234396 A1   Oct. 20, 2005

(51) Int. Cl.
 *A61M 25/00* (2006.01)
(52) U.S. Cl. ...................................... 604/523
(58) Field of Classification Search ......... 604/523–539, 604/264–279, 43, 284; 606/108, 191–194
 See application file for complete search history.

(56) References Cited

U.S. PATENT DOCUMENTS

| | | | | |
|---|---|---|---|---|
| 4,317,445 A | | 3/1982 | Robinson ................. 128/214.4 |
| 4,406,656 A | * | 9/1983 | Hattler et al. ............... 604/523 |
| 5,282,827 A | | 2/1994 | Kensey et al. ............... 606/215 |
| 5,290,310 A | | 3/1994 | Makower et al. ............ 606/213 |
| 5,292,332 A | | 3/1994 | Lee ............................ 606/213 |
| 5,411,520 A | | 5/1995 | Nash et al. ................... 606/213 |
| 5,431,639 A | | 7/1995 | Shaw ......................... 604/264 |
| 5,437,631 A | | 8/1995 | Janzen ........................ 604/49 |
| 5,443,481 A | | 8/1995 | Lee ............................ 606/213 |
| 5,486,195 A | | 1/1996 | Myers et al. ................. 606/213 |
| 5,613,974 A | | 3/1997 | Andreas et al. ............. 606/144 |
| 5,643,318 A | * | 7/1997 | Tsukernik et al. ........... 606/214 |
| 5,645,566 A | | 7/1997 | Brenneman ................. 606/213 |
| 5,695,457 A | * | 12/1997 | St. Goar et al. ............ 604/4.01 |
| 5,707,393 A | | 1/1998 | Kensey et al. ............... 606/213 |
| 5,755,727 A | | 5/1998 | Kontos ........................ 606/144 |
| 5,810,810 A | | 9/1998 | Tay et al. ...................... 606/50 |
| 5,814,065 A | | 9/1998 | Diaz .......................... 606/213 |
| 5,868,717 A | * | 2/1999 | Prosl ........................... 604/264 |
| 5,935,147 A | | 8/1999 | Kensey et al. ............... 606/213 |
| 6,004,310 A | * | 12/1999 | Bardsley et al. ............. 604/524 |
| 6,022,372 A | | 2/2000 | Kontos ........................ 606/219 |
| 6,090,130 A | | 7/2000 | Nash et al. ................... 606/213 |
| 6,162,192 A | | 12/2000 | Cragg et al. .................. 604/15 |
| 6,179,863 B1 | | 1/2001 | Kensey et al. ............... 606/215 |
| 6,193,670 B1 | | 2/2001 | Van Tassel et al. .......... 600/486 |
| 6,231,561 B1 | | 5/2001 | Frazier et al. ............... 604/500 |
| 6,270,477 B1 | * | 8/2001 | Bagaoisan et al. ....... 604/96.01 |
| 6,682,489 B2 | | 1/2004 | Tenerz et al. ................ 600/485 |

\* cited by examiner

*Primary Examiner*—Manuel A Mendez
(74) *Attorney, Agent, or Firm*—Holland & Hart

(57) ABSTRACT

The present invention provides a vascular insertion sheath with collapsible penetration locators. The collapsible penetration locators provide the insertion sheath with a small outer diameter and the added functionality of precise location indicator. The collapsible penetration locators comprise thin membranes that collapse upon insertion of a sealing device or vascular instrument into the insertion sheath. The insertion sheath includes a reinforced wall according to some embodiments, with a coiled or braided filament for reinforcement.

28 Claims, 6 Drawing Sheets

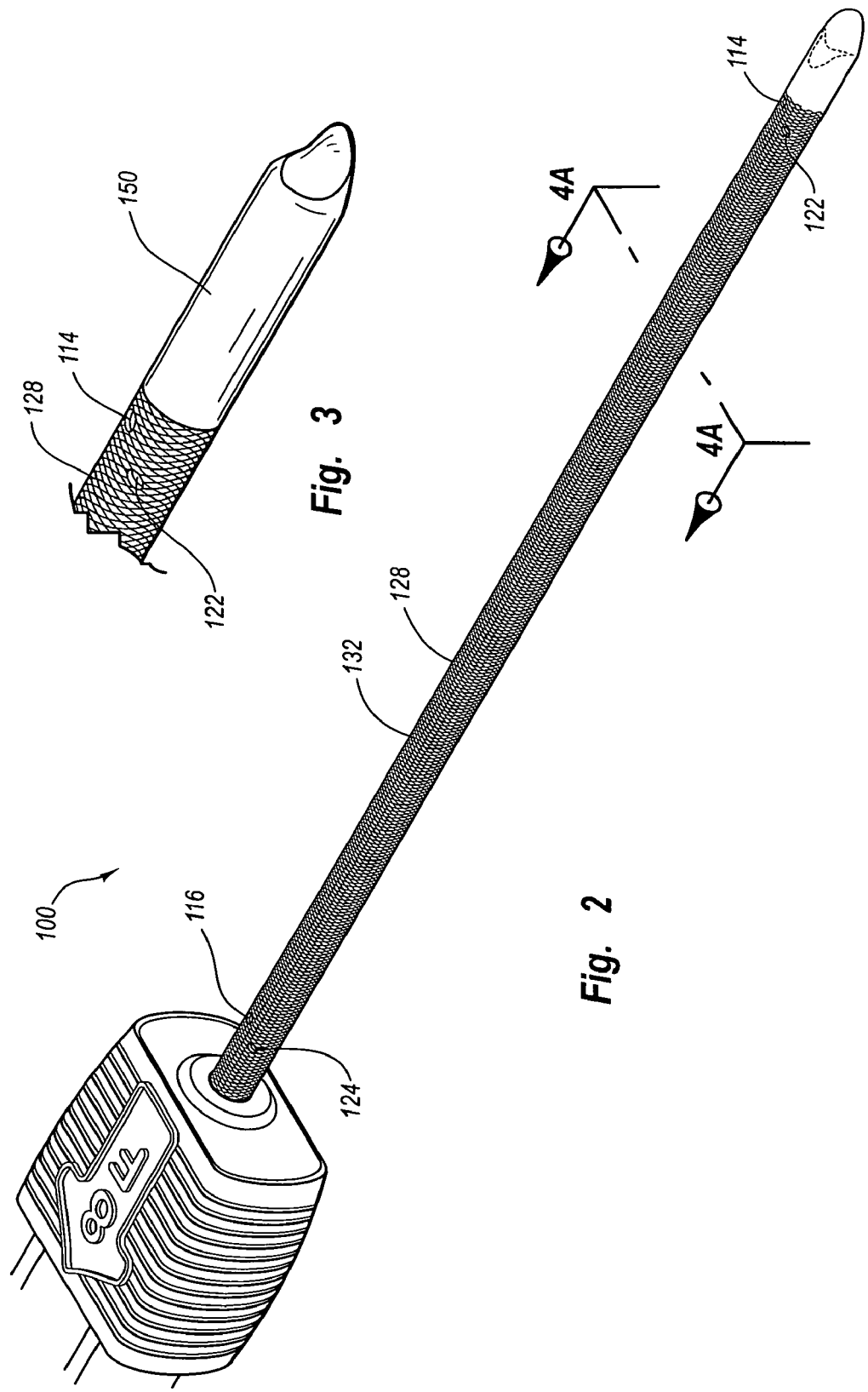

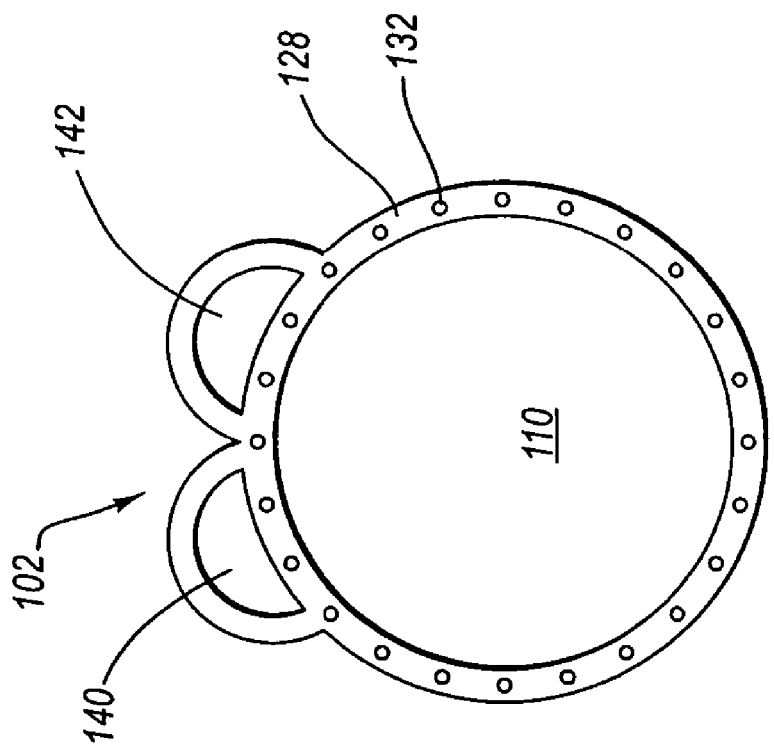
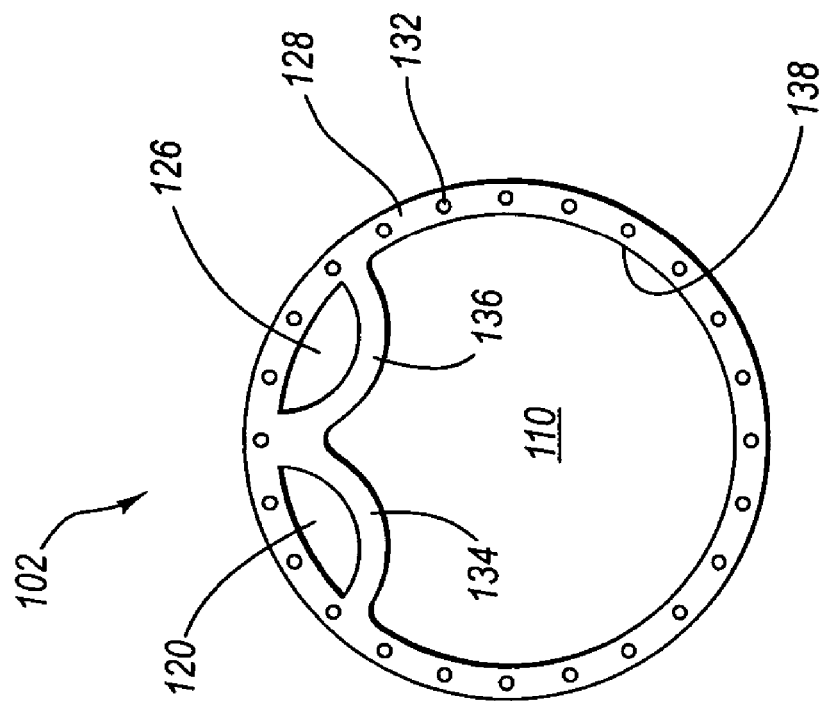

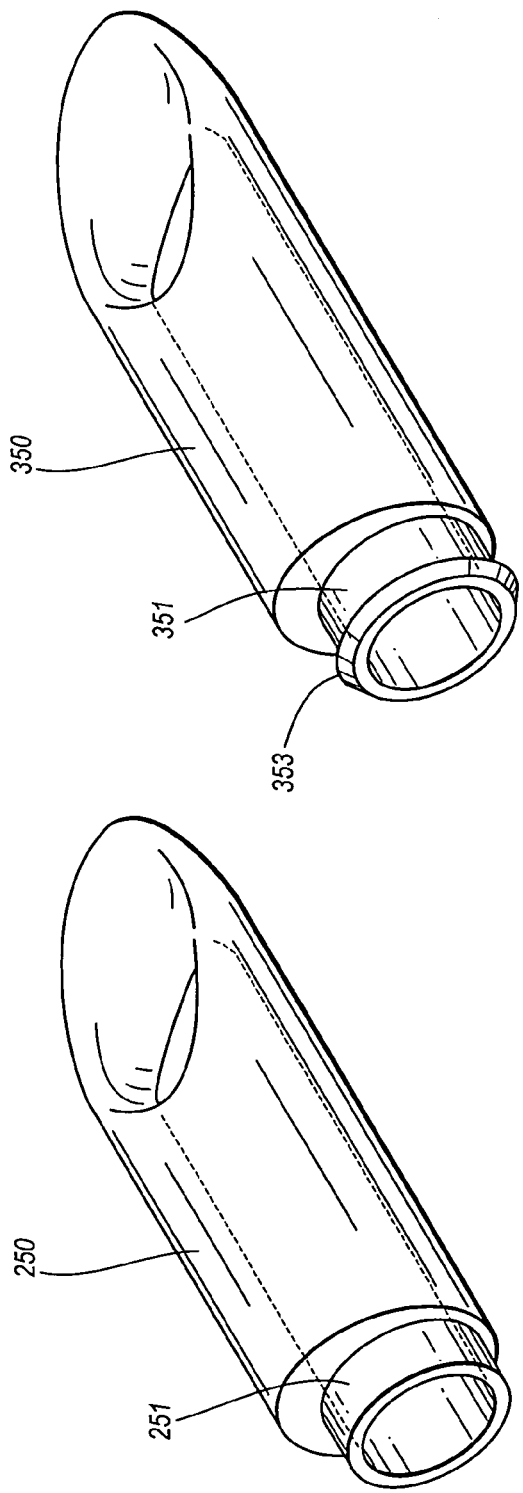
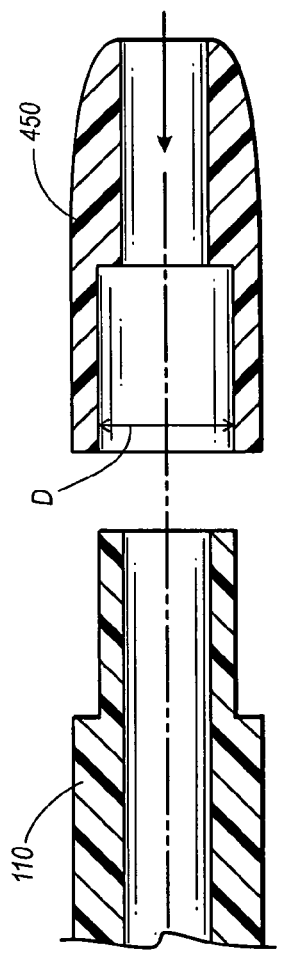
Fig. 7A  Fig. 7B
Fig. 8

METHOD AND APPARATUS FOR LOCATING VASCULAR PUNCTURES

FIELD OF THE INVENTION

The present invention relates to medical devices, and, more particularly, to a vascular insertion device with a collapsible puncture-locating lumen.

BACKGROUND OF THE INVENTION

Various medical procedures, particularly cardiology procedures, involve accessing a corporeal vessel or other lumen through a percutaneous insertion sheath. The insertion sheath necessarily requires the formation of a hole or opening in the vessel wall so that a medical procedure can be performed via the insertion sheath. After the particular medical procedure has been performed, the insertion sheath must eventually be removed from the vessel and the access hole in the vessel wall must be closed.

A number of prior vascular closure devices have been developed to close the vessel wall. Closing the vessel wall typically involves packing a resorbable sealing plug at the hole or sandwiching the hole between the sealing plug and an anchor. Examples of prior vascular closure devices are described in U.S. Pat. Nos. 6,179,863; 6,090,130; and 6,045,569 and related patents that are hereby incorporated by reference.

However, prior to a successful deployment of the sealing plug or another vascular tool, the insertion sheath must be properly located within the vessel or other lumen. Proper placement of the insertion sheath enables proper placement of the sealing plug or insertion of a vascular tool.

According to conventional techniques, proper placement of the insertion sheath is accomplished with the aid of a puncture locator. Typically a puncture locator and the insertion sheath are inserted through the hole in the vessel wall. The puncture locator provides a fluid communication path from a distal orifice (where the insertion sheath enters the vessel) to a proximal end, where blood flow can be observed by an operator. As the insertion sheath puncture locator assembly penetrates the vessel wall, blood flows through and out of the puncture locator. Blood exiting the puncture locator indicates that the insertion sheath has begun to penetrate the blood vessel. Blood will continue to flow through the puncture locator until the insertion sheath and/or the puncture locator are removed from the vessel.

While the puncture locator is usually helpful for properly positioning the insertion sheath, the use of the puncture locator is only a secondary indication of insertion sheath position. The blood flow through the puncture locator is an actual indication of the position of the puncture locator, and the relative positions of the puncture locator and the insertion sheath provide secondary indication of the location of the insertion sheath. The use of a separate puncture locator relies on the orientation of the puncture locator with respect to the insertion sheath. In addition, the use of the puncture locator adds an additional step to the process of positioning the insertion sheath. Moreover, once the puncture locator is removed from the insertion sheath, any movement of the insertion sheath out of position is not likely to be detected. It would be desirable to include one or more locating lumens in the insertion sheath. Providing locating lumens in the insertion sheath would provide direct indication of insertion sheath position, and facilitate detection of any subsequent mispositioning. However, it is not desirable to increase the outer diameter of current insertion sheaths beyond 6F and 8F sizes. A larger outer diameter requires a larger puncture, and a larger puncture is more difficult to close.

The present invention is directed to overcoming, or at least reducing the effects of, one or more of the problems outlined above.

SUMMARY OF THE INVENTION

In one of many possible embodiments, the present invention provides an insertion apparatus comprising a vascular insertion sheath. The vascular insertion sheath includes a first flexible lumen and a first collapsible lumen having a diameter smaller than the first flexible lumen. The first collapsible lumen is a puncture locating lumen for indicating a position of the vascular insertion sheath within a blood vessel. The first flexible lumen comprises a thin, reinforced wall. It is desirable to maintain a thin wall while also adding the precise locating functionality afforded by the puncture locating lumen. Therefore, the first flexible lumen may be reinforced with a coiled, braided, or randomly oriented filaments. For example, the coil or braids may comprise strands of stainless steel, carbon fiber, aramid fiber, or Kevlar® fiber. The first flexible lumen may terminate distally with a tip portion that is not filament-reinforced.

According to some embodiments, the first collapsible lumen is contained within an outer diameter of the first flexible lumen, although according to other embodiments the collapsible lumen protrudes outside of the first flexible lumen. Some embodiments include at least a second collapsible lumen having a diameter smaller than the first flexible lumen. The first and second collapsible lumens comprises separate fluid inlet and outlet ports to give precise indication of the location of the vascular insertion sheath by a visual fluid flow. The first and second collapsible lumens collapse in response to insertion of a dilator, a sealing device, or other instrument into the first flexible lumen.

According to another aspect of the invention, there is a vascular insertion sheath comprising an elongated shaft having an outer diameter and a reinforced wall. The insertion sheath also includes a primary lumen extending through the elongated shaft and a first collapsible lumen extending at least partially through the elongated shaft. The first collapsible lumen comprises a membrane protruding from an inner or outer diameter of the elongated shaft, and the reinforced wall includes braided or coiled filaments. According to some embodiments, the reinforced wall is less than 0.010 inches thick, preferably less than about 0.007 inches thick. A non-reinforced tip may be attached to the elongated shaft. According to some embodiments, there is a second collapsible lumen extending at least partially through the elongated shaft as well.

According to another aspect of the invention, there is a vascular insertion apparatus comprising a tissue puncture sealing device and an insertion sheath receptive of the tissue puncture sealing device. The insertion sheath includes a wall less than about 0.010 inches thick and a first collapsible locating lumen. The collapsible locating lumen collapses in response to insertion of the tissue puncture sealing device into the insertion sheath. The insertion sheath may also include at least a second collapsible locating lumen.

Another aspect of the invention provides a vascular insertion assembly comprising an insertion sheath having a distal end, a proximal end, and an inside diameter. The assembly also includes a collapsible puncture locating lumen within the inside diameter of the insertion sheath, the puncture locating lumen also having a distal end and a proximal end. The distal end of the insertion sheath includes a first inlet port in fluid communication with a first outlet port via the collapsible puncture locating lumen for providing visual indication of insertion sheath location by a flow of blood. The assembly may further include a second collapsible puncture locating lumen having a distal end and a proximal end, a second inlet port located at the distal end of the insertion sheath, and a second outlet port in fluid communication with the second inlet port via the second collapsible puncture locating lumen for providing another indication of insertion sheath location by a flow of blood.

Another aspect of the invention provides a method of making a vascular insertion sheath. The method includes providing a hollow, flexible plastic shaft having a total wall thickness of less than about 0.010 and at least one collapsible locating lumen, reinforcing the hollow, flexible plastic shaft with one or more filaments, and attaching a tip to a distal end of the hollow, flexible plastic shaft. The method may include coiling or braiding the filament around the hollow, flexible plastic shaft such that the total wall thickness remains less than about 0.010 inches. The method may include providing at least two collapsible locating lumens in the hollow, flexible plastic shaft.

Another aspect of the invention provides a tissue puncture closure assembly for partial insertion into and sealing of an internal tissue wall puncture comprising a filament extending from a first end of a closure device to a second end of the closure device, an anchor for insertion through the tissue wall puncture attached to the filament at the second end of the closure device, a sealing plug slidingly attached to the filament adjacent to the anchor, and an insertion sheath receptive of the closure device and including a plurality of collapsible locating lumens.

The foregoing and other features, utilities and advantages of the invention will be apparent from the following more particular description of preferred embodiments of the invention as illustrated in the accompanying drawings.

BRIEF DESCRIPTION OF THE DRAWING

The accompanying drawings illustrate various embodiments of the present invention and are a part of the specification. The illustrated embodiments are merely examples of the present invention and do not limit the scope of the invention.

FIG. 2 is a detailed perspective view of an insertion sheath according to another embodiment of the present invention.

FIG. 3 is a detailed perspective view of an end portion of the insertion sheath from an opposite side shown in FIG. 2.

FIG. 4A is a cross-sectional side view of an insertion sheath according to one embodiment of the present invention with internal collapsible locating lumens.

FIG. 4B is a cross-sectional side view of an insertion sheath according to another embodiment of the present invention with external locating lumens.

FIG. 7A is a perspective view of a tip portion of the insertion sheath of FIG. 1 according to another embodiment of the present invention.

FIG. 7B is a perspective view of a tip portion of the insertion sheath of FIG. 1 according to another embodiment of the present invention.

FIG. 8 is a cross-sectional side view a tip portion of of the insertion sheath of FIG. 1 according to another embodiment of the present invention.

Throughout the drawings, identical reference numbers designate similar, but not necessarily identical, elements

DETAILED DESCRIPTION

As mentioned above, vascular procedures are commonly performed throughout the world and require access to a bodily lumen through a puncture. Often an insertion sheath or insertion sheath is placed in the puncture to facilitate access to the lumen by one or more vascular instruments, including puncture closure devices when the vascular procedure is completed. Typically, the location of an artery or other lumen is indicated by a flow of blood through a puncture locator as the instrument enters the artery. The present invention describes methods and apparatus for integrating puncture locating with the insertion sheath, while minimizing the outer diameter of the insertion sheath. Although the vascular instruments shown and described below include a particular puncture sealing device, the application of the principles described herein to an insertion sheath is not limited to any specific devices. The principles described herein may be used with any vascular device, particularly vascular devices used to locate an artery. Therefore, while the description below is directed primarily to arterial procedures and the fluid referenced most often is blood flowing through an artery, the method and apparatus may be used according to principles described herein to properly position any instrument in a blood vessel or other bodily lumen.

As used throughout the claims and specification the term "insertion sheath" is used broadly to encompass any device used to facilitate introduction of vascular instruments into a blood vessel or other bodily lumen. The term "fluid" refers to any substance whose molecules move freely past one another and that has the tendency to assume the shape of its container, including both liquids and gasses. A "lumen" refers to an open space, cavity, or fluid flow passage. The words "including" and "having," as used in the specification, including the claims, have the same meaning as the word "comprising."

Figure 1:
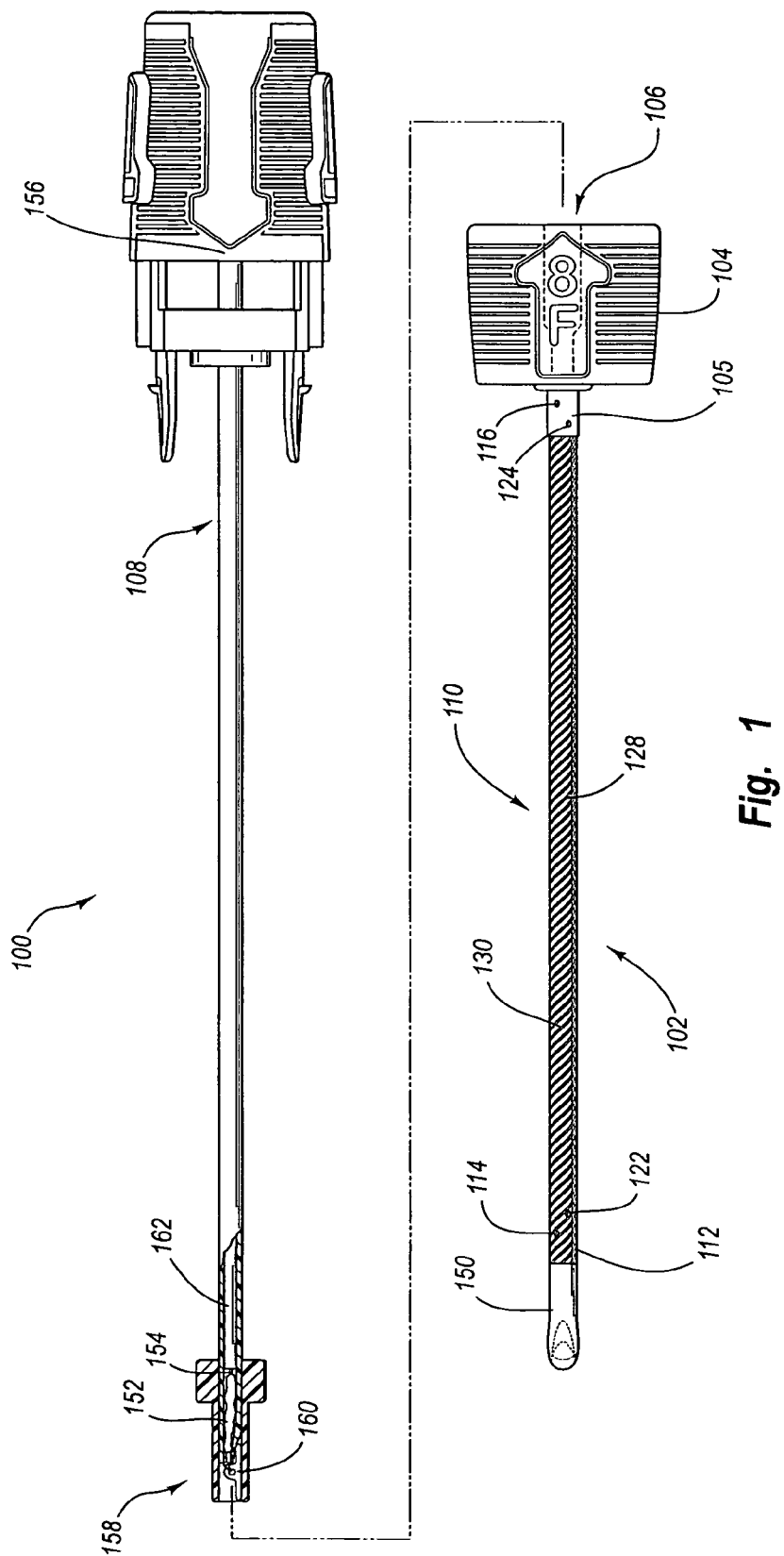
FIG. 1 is a perspective assembly view of an insertion sheath with collapsible locating lumens and a tissue puncture sealing device according to one embodiment of the present invention.

Referring now to the drawings, and in particular to FIG. 1, a vascular insertion assembly or apparatus 100 according to one embodiment of the present invention is shown. According to the embodiment of FIG. 1, the vascular insertion apparatus 100 includes a vascular insertion sheath or insertion sheath 102 with a hub 104 disposed at a proximal end 105 thereof. The insertion sheath 102 provides access to an artery or other vessel via an inside diameter 106 that is receptive of a tissue puncture sealing device 108 or other vascular instrument (e.g. as a dilator).

The insertion sheath 102 includes a primary or first flexible lumen 110. The first flexible lumen 110 comprises an elongated, hollow, shaft with a reinforced wall 128. The reinforced wall 128 is shown in cross section in FIGS. 4A-5C. The reinforced wall 128 is preferably plastic with a filament reinforcement to provide a thin wall thickness while resisting kinking, particularly as the insertion sheath 102 is inserted into a puncture. For example, according to the embodiment of FIG. 1, the reinforced wall 128 comprises a coiled filament 130. The coiled filament 130 extends substantially along a length of the first flexible lumen 110 as shown. However, according to other embodiments the coiled filament extends along the full length of the first flexible lumen 110. The coiled filament 130 may comprise any of a number of materials including, but not limited to: stainless steel, carbon fiber, aramid fiber, and Kevlar® fiber. The filament 130 may also comprise a flat ribbon coil.

According to the embodiment of FIG. 1, a preformed tip 150 is attached at a distal end 112 to the first flexible lumen 110. The preformed tip 150 is preferably flexible, but may also be rigid according to some embodiments. The preformed tip 150 is preferably plastic and is not reinforced. The preformed tip 150 is shown in more detail in an assembly view in FIG. 6.

Although the embodiment of FIG. 1 includes the preformed tip 150, other embodiments of the insertion sheath 102 may not include a separately formed tip. In addition, according to the embodiment of FIG. 2, another filament configuration strengthens the reinforced wall 128.

The reinforced wall 128 of FIG. 2 comprises a braid-reinforced wall. A braided filament 132 provides the reinforcement. The braided filament 132 may comprise any of the same materials listed above for the coiled filament 130 (FIG. 1) including, but not limited to: stainless steel, carbon fiber, aramid fiber, and Kevlar® fiber. The braided filament 132 may also comprise a flat ribbon braid. FIG. 3 shows a close-up of the preformed tip 150 with the reinforced wall 128. The reinforced wall 128 may include other reinforcing configurations as well, and is not limited to the coiled and braided structures shown.

Referring again to FIG. 1, the insertion sheath 102 must be properly positioned in a puncture to facilitate insertion of the tissue puncture sealing device 108 or other vascular instruments. Historically, the insertion sheath 102 is positioned with the aid of a puncture locator that is inserted through the insertion sheath and later removed as described above. However, according to principles of the present invention, the insertion sheath 102 includes and at least one locating lumen that eliminates the need for a separate puncture locator. The at least one locating lumen may comprise any of a number of shapes and configurations, several examples of which are shown and discussed below with reference to FIGS. 4A-5C. As shown in FIG. 1, however, a first of the at least one locating lumens opens at the distal end 112 of the first flexible lumen 110 to a first inlet port 114. The first inlet port 114 is in fluid communication with a first outlet port 116 via a first collapsible lumen 120 (FIG. 4A) extending at least partially through the first flexible lumen 110. Similarly, a second of the at least one locating lumens opens near the distal end 112 of the first flexible lumen 110 to a second inlet port 122. The second inlet port 122 is spaced proximally from the first inlet port 114 to provide more precise indication of the location of the insertion sheath within a blood vessel. The second inlet port 122 is in fluid communication with a second outlet port 124 via a second collapsible lumen 126 (FIG. 4A) extending at least partially though the first flexible lumen 110. The second outlet port 122 is spaced from the first outlet port 116 to enable a user to distinguish between fluid flows exiting through each port.

Accordingly, as the first flexible lumen 110 of the insertion sheath 102 is inserted through a percutaneous incision, through a vessel puncture, and ultimately into a blood vessel, a flow of blood will exit through the first outlet 116 when the first inlet port 114 enters the blood vessel and is exposed to a blood stream. The blood flow through the first outlet port 116 provides a first visual indication of the location of first flexible lumen 110. Normally, when the first inlet 114 is exposed to the blood stream of an artery, blood spurts from the first outlet 116 in a pattern corresponding to a patient's heartbeat. If the insertion sheath 102 is advanced further into the blood vessel, a second flow of blood will pass out of the second outlet 124 when the second inlet port 122 enters the blood vessel. According to some embodiments, the insertion sheath 102 may be retracted after blood flow is observed through the second outlet port 124 until the blood flow therethrough ceases. A flow of blood through only the first outlet port 116 may, according to some embodiments, indicate proper positioning of the insertion sheath 102 partially within the blood vessel. It will be appreciated by those of skill in the art having the benefit of this disclosure, however, that additional or fewer lumens having separate inlet and outlet ports may also be employed with the insertion sheath 102 as desired.

By adding at least one locating lumen to the insertion sheath 102, a user has an advantage over the typical locating procedures that require a separate puncture locator. Providing a locating lumen to the insertion sheath 102 directly indicates insertion sheath 102 location. In addition, a shift in the insertion sheath's position is much less likely to go unnoticed according to the present invention. If the insertion sheath 102 moves out of its proper position, blood flow through the first outlet port 116 will cease, or blood will begin to flow through the second outlet port 124. However, it may be undesirable to add to the outer diameter of the first flexible lumen 110 to provide room for the first and second collapsible lumens 120, 126 (FIG. 4A).

Therefore, according to some embodiments of the present invention, the first flexible lumen 110 has the reinforced wall 128 shown in FIGS. 2A-2B that is thinner than conventional insertion sheath walls to accommodate at least one locator lumen without significantly increasing the outside diameter of the first flexible lumen 110. FIGS. 4A-4B, FIGS. 5A-5C, and the corresponding descriptions below describe several embodiments of the first flexible lumen 110 and the use one or more locator lumens.

Referring to FIG. 4A, according to some embodiments, the reinforced wall 128 is less than 0.010 inches thick. However, according to other embodiments, the reinforced wall 128 is no more than about 0.007 to 0.008 inches thick, and according to still other embodiments the reinforced wall 128 is no more than about 0.006 inches thick. A wall thickness of less than 0.010 inches is less than conventional wall thicknesses for an insertion sheath, and facilitates maintaining a standard or near-standard outer diameter while adding locating lumens.

According to the embodiment of FIG. 4A, the reinforced wall 128 comprises the braided filament 132, but the coiled filament 130 (FIG. 1) or other reinforcing filaments may also be used. The reinforced wall 128, including the reinforcing braided filament 132, comprises the small wall thickness dimensions mentioned above.

FIG. 4A illustrates the first and second collapsible lumens 120, 126 mentioned above with reference to FIG. 1. According to FIG. 4A, the first and second collapsible lumens 120, 126 have smaller diameters than the first flexible lumen 110. The first and second collapsible lumens 120, 126 comprise first and second membranes 134, 136, respectively, protruding from an inner diameter 138 of the first flexible lumen 110.

The first and second membranes 134, 136 are preferably plastic and co-extruded with the first flexible lumen 110. The first and second membranes 134, 136 will generally maintain the shape shown absent any external forces. However, the first and second membranes 134, 136 readily collapse in response to insertion of a vascular instrument such as the tissue puncture sealing device 108 (FIG. 1) into the first flexible lumen 110. Therefore, the insertion sheath 102 of FIG. 1 maintains a standard outer diameter consistent with a 6F or 8F size, and adds puncture locating capability by including the first and second collapsible lumens 120, 126.

Alternative to the embodiment shown in FIG. 4A, the first and second collapsible lumens 120, 126 may be replaced by first and second external locating lumens 140, 142 as shown in FIG. 4B. The first and second external locating lumens 140, 142 are preferably rigid enough to maintain the shape shown when inserted through a puncture. The configuration shown in FIG. 2B facilitates a standard 6F or 8F size for the insertion sheath 102 with a minimal addition to the outer diameter represented by the first and second external locating lumens 140, 142.

Figure 5C:
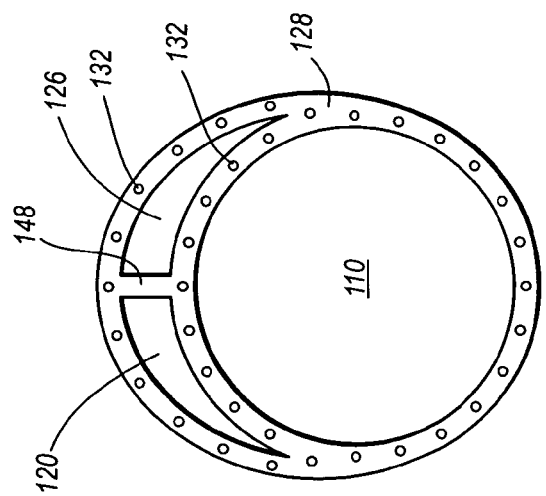
FIG. 5C is a cross-sectional side view of an insertion sheath according to another embodiment of the present invention with internal locating lumens and internal and external wall reinforcement.
Figure 5B:
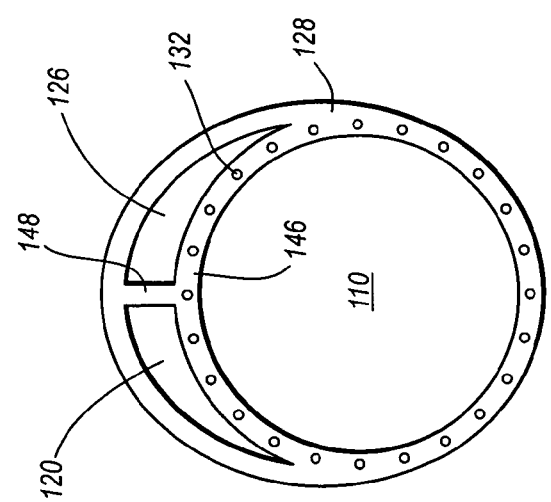
FIG. 5B is a cross-sectional side view of an insertion sheath according to another embodiment of the present invention with internal locating lumens and internal wall reinforcement.
Figure 5A:
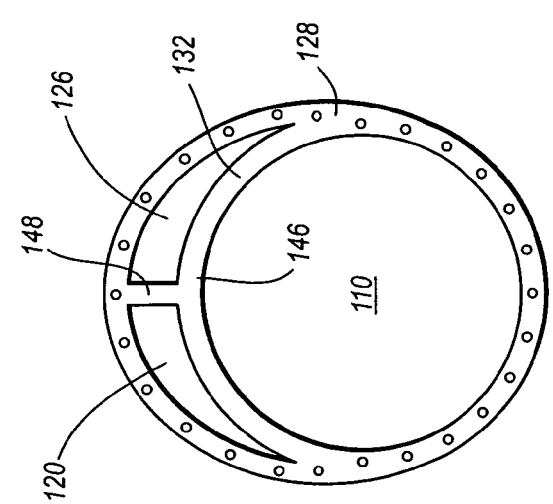
FIG. 5A is a cross-sectional side view of an insertion sheath according to another embodiment of the present invention with internal locating lumens and external wall reinforcement.

The locating lumens 120, 126, 140, 142 shown in FIGS. 4A-4B may comprise other alternative structures as well, for example the configurations shown in FIGS. 5A-5C. According to the embodiment of FIG. 4A, an outer diameter of the reinforced wall 128 is slightly elliptical, rather than strictly circular. The first flexible lumen 110 is generally circular, and the first and second collapsible lumens 120, 126 are internal to the reinforced wall 128 defined by the outer diameter of the ellipse. An internal portion 146 of the first flexible lumen 110 is not reinforced and therefore a neck 148 separating the first and second collapsible lumens 120, 126 may buckle upon insertion of a vascular instrument into the first flexible lumen 110 and cause the first and second collapsible lumens 120, 126 to collapse. However, according to some embodiments, the insertion of a vascular instrument into the first flexible lumen 110 may have no effect on the shape of the first and second collapsible lumens 120, 126. The elliptical outer diameter shown in FIGS. 5A-5C provides spacing for the first and second collapsible lumens 120, 126 with only a minimal increase in outer diameter or surface area as compared to a typical circular outer diameter.

According to some embodiments, the reinforced wall 128 does not extend around the first and second collapsible lumens 120, 126. Instead, as shown in FIG. 5B, the reinforcing filament 132 encloses the generally circular first flexible lumen 110, including the internal portion 146. According to other embodiments, however, the reinforcing filament 132 reinforces both the outer elliptical diameter and the internal portion 146 as shown in FIG. 5C. The first and second collapsible lumens 120, 126 may be less likely to collapse upon insertion of a vascular instrument into the first flexible lumen 110 according to the embodiments of FIGS. 5B and 5C than the embodiment of FIG. 5A because of the reinforcement along the internal portion 146. Nevertheless, the neck 148 may buckle and cause the first and second collapsible lumens 120, 126 to collapse when a sufficient internal force is applied to the first flexible lumen 110.

Figure 6:
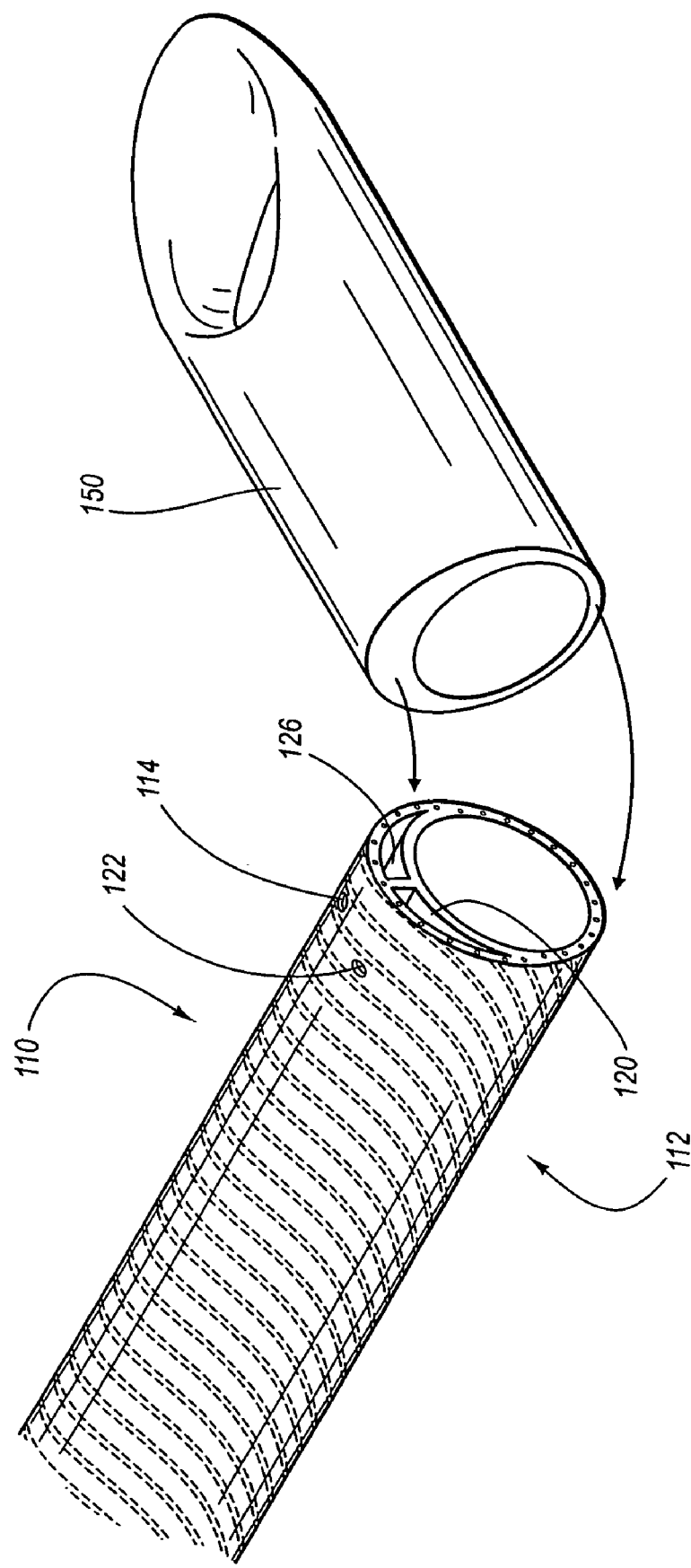
FIG. 6 is detailed perspective view of an end portion the insertion sheath of FIG. 1 with a bonded tip disassembled from the insertion sheath.

The embodiment of FIG. 5A is shown in FIG. 6 in a perspective view wherein the preformed tip 150 is disassembled from the first flexible lumen 110. According to the embodiment of FIG. 6, the preformed tip is bonded to first flexible lumen 110 at the distal end 112. The preformed tip 150 includes a wall thickness that varies so as to close the first and second collapsible lumens 120, 126 at the distal end 112. Accordingly, as discussed in more detail above, when either or both of the first and second inlet ports 114, 122 is exposed to a fluid stream, fluid will flow into the inlet ports 114, 122, through the collapsible lumens 120, 126, and out of the outlet ports 116, 124 (FIG. 1). Therefore, punctures may be located without the aid of a separate puncture locator, and any changes in the insertion sheath's position are readily discerned.

Although the preformed tip 150 shown in FIG. 6 is bonded to the first flexible lumen 110, other embodiments are also contemplated. For example, in one preferred embodiment shown in FIG. 7A, a preformed tip 250 includes generally circular protrusion 251 having a diameter substantially the same as or slightly greater than the diameter of the first flexible lumen 110 (FIG. 6). The preformed tip 250 of FIG. 7A may therefore be partially inserted into the first flexible lumen 110 (FIG. 6) to form a lap joint therebetween. Another embodiment shown in FIG. 7B is a preformed tip 350 with a generally circular protrusion 351 and a tapered ridge 353. As with the embodiment shown in FIG. 7A, the preformed tip 350 may be partially inserted into the first flexible lumen 110 (FIG. 6) to form a lap joint. Further, the tapered ridge may provide sufficient hoop stress in the first flexible lumen 110 (FIG. 6) to securely attach the preformed tip 350 to the first flexible lumen 110 (FIG. 6).

Alternatively, as shown in FIG. 8, a preformed tip 450 may be sized to fit over the first flexible lumen 110. According to the embodiment of FIG. 8, a reverse lap joint if formed as the preformed tip 450 slides over the first flexible lumen 110. The first flexible lumen 110 may be stepped down to a smaller outer diameter as shown, and/or an internal diameter D of the preformed tip 450 may step up as shown. The steps in diameter for the preformed tip 450 and/or the first flexible lumen 110 facilitate a flush arrangement therebetween.

As mentioned above, one of the uses of the insertion sheath 102 is to provide the tissue puncture sealing device 108 (FIG. 1) access to a tissue puncture. As shown in FIG. 1, in order to facilitate deployment of a sealing plug 152, the tissue puncture closure device 108 may include a filament 154 extending from a first or proximal end 156 of the tissue puncture closure device 108 to a second or distal end 158 of the tissue puncture closure device 108. The tissue puncture closure device 108 also includes an anchor 160 for insertion through a tissue wall puncture, through which the filament 154 is threaded at the second end 158 of the closure device 108. The sealing plug 152 is slidingly attached to the filament 154 adjacent to the anchor 160. The sealing plug 152 may be automatically or manually tamped with a tamping tube 162. Tamping the sealing plug 152 sandwiches the puncture between the anchor 160 and the sealing plug 152. The filament 154 may then be tied and/or cut, and the closure device 108 and insertion sheath 102 may be removed. Accordingly, a puncture may be located and sealed according to the present invention without the aid of a separate puncture locator.

While the invention has been particularly shown and described with reference to embodiments thereof, it will be understood by those skilled in the art that various other changes in the form and details may be made without departing from the scope of the invention.

What is claimed is:

1. A vascular insertion apparatus, comprising:
   a vascular insertion sheath, the vascular insertion sheath comprising:
   a first flexible lumen; and
   a first collapsible lumen having a diameter that is smaller than a diameter of the first flexible lumen, the first collapsible lumen being open to fluid flow without application of an external force and collapsible upon insertion of a vascular device in the first flexible lumen.

2. A vascular insertion apparatus according to claim 1 wherein the first collapsible lumen comprises a puncture locating lumen for indicating a position of the vascular insertion sheath within a blood vessel.

3. A vascular insertion apparatus according to claim 1 wherein the first flexible lumen comprises a flexible coil-reinforced wall.

4. A vascular insertion apparatus according to claim 1 wherein the first flexible lumen comprises a flexible braided wall.

5. A vascular insertion apparatus according to claim 1 wherein the first flexible lumen comprises a flexible braided wall, the braided wall comprising strands of one or more of: stainless steel, carbon fiber, aramid fiber, and Kevlar® fiber.

6. A vascular insertion apparatus according to claim 1 wherein the first flexible lumen comprises a flexible braided wall, the flexible braided wall comprising a flat ribbon braid.

7. A vascular insertion apparatus according to claim 1 wherein the first collapsible lumen is contained within an outer diameter of the first flexible lumen.

8. A vascular insertion apparatus according to claim 1, further comprising a second collapsible lumen having a diameter smaller than the first flexible lumen.

9. A vascular insertion apparatus according to claim 1, further comprising a second collapsible lumen having a diameter that is smaller than a diameter of the first flexible lumen, wherein the second collapsible lumen is contained within an outer diameter of the first flexible lumen.

10. A vascular insertion apparatus according to claim 8 wherein the first flexible lumen comprises a distal end, and wherein the first and second collapsible lumens extend substantially to the distal end, and the second collapsible lumen opens at a position proximal of an opening of the first collapsible lumen.

11. A vascular insertion apparatus according to claim 8 wherein the first and second collapsible lumens each open to separate, spaced fluid outlet ports in the first flexible lumen.

12. A vascular insertion apparatus according to claim 1 wherein the first flexible lumen comprises a flexible coil-reinforced wall with a bonded tip portion.

13. A vascular insertion apparatus according to claim 1 wherein the first flexible lumen comprises a flexible braided wall with a bonded tip portion.

14. A vascular insertion apparatus according to claim 1 wherein the first collapsible lumen collapses in response to insertion of a dilator or sealing device into the first flexible lumen.

15. A vascular insertion apparatus according to claim 1 wherein the first collapsible lumen is external to an outer diameter of the first flexible lumen.

16. A vascular insertion sheath, comprising:
an elongated shaft having an outer diameter and a reinforced wall;
a primary lumen extending through the elongated shaft;
a first collapsible lumen extending at least partially through the elongated shaft, the first collapsible lumen being open to fluid flow without application of an external force and collapsible upon insertion of a vascular device in the primary lumen.

17. A vascular insertion sheath according to claim 16, further comprising a second collapsible lumen extending at least partially through the elongated shaft.

18. A vascular insertion sheath according to claim 16 wherein the first collapsible lumen comprises a membrane protruding from an inner diameter of the elongated shaft.

19. A vascular insertion sheath according to claim 16 wherein the reinforced wall comprises braided filaments.

20. A vascular insertion sheath according to claim 16 wherein the reinforced wall is less than 0.010 inches thick.

21. A vascular insertion sheath according to claim 16 wherein the reinforced wall comprises coiled filament.

22. A vascular insertion sheath according to claim 16 wherein the reinforced wall is less than about 0.007 inches thick.

23. A vascular insertion sheath according to claim 16 wherein the reinforced wall is less than about 0.006 inches thick.

24. A vascular insertion sheath according to claim 16, further comprising a tip bonded to the elongated shaft.

25. A vascular insertion sheath according to claim 16 wherein the first collapsible lumen comprises a membrane protruding from an outer diameter of the elongated shaft.

26. A vascular insertion sheath according to claim 16 wherein the outer diameter comprises an ellipse.

27. A vascular insertion sheath according to claim 16 wherein the reinforced wall is reinforced around the outer diameter.

28. A vascular insertion sheath according to claim 16 wherein the reinforced wall is reinforced around an inner diameter, and wherein the first collapsible lumen is external to the inner diameter.

* * * * *